US009345836B2

(12) United States Patent
Cabiri et al.

(10) Patent No.: US 9,345,836 B2
(45) Date of Patent: May 24, 2016

(54) DISENGAGEMENT RESISTANT TELESCOPING ASSEMBLY AND UNIDIRECTIONAL METHOD OF ASSEMBLY FOR SUCH

(71) Applicant: MEDIMOP Medical Projects Ltd., Ra'anana (IL)

(72) Inventors: Oz Cabiri, Macabim-Reut (IL); Reuven Y. Filman, Netanya (IL); Yossi Bar-El, Beit Arye (IL)

(73) Assignee: Medimop Medical Projects Ltd., Ra'anana (IL)

( * ) Notice: Subject to any disclaimer, the term of this patent is extended or adjusted under 35 U.S.C. 154(b) by 325 days.

(21) Appl. No.: 13/874,085

(22) Filed: Apr. 30, 2013

(65) Prior Publication Data
US 2013/0304021 A1   Nov. 14, 2013

(51) Int. Cl.
| | |
|---|---|
| *A61M 5/315* | (2006.01) |
| *A61M 5/145* | (2006.01) |
| *F16H 25/20* | (2006.01) |
| *A61M 5/142* | (2006.01) |
| *A61M 5/14* | (2006.01) |

(Continued)

(52) U.S. Cl.
CPC ....... *A61M 5/31511* (2013.01); *A61M 5/14248* (2013.01); *A61M 5/14566* (2013.01); *F16H 25/2056* (2013.01); *A61M 5/1413* (2013.01); *A61M 5/16827* (2013.01); *A61M 5/1723* (2013.01); *A61M 2005/1426* (2013.01); *A61M 2005/14252* (2013.01); *A61M 2005/14268* (2013.01); *A61M 2005/31518* (2013.01); *A61M 2205/3523* (2013.01); *A61M 2205/3569* (2013.01); *Y10T 29/49826* (2015.01)

(58) Field of Classification Search
CPC .................... A61M 5/14566; A61M 5/31558; A61M 5/315; A61M 5/31543
See application file for complete search history.

(56) References Cited

U.S. PATENT DOCUMENTS

| | | | |
|---|---|---|---|
| 1,795,630 | A | 3/1931 | Wilson |
| 2,860,635 | A | 11/1958 | Wilburn |
| 3,203,269 | A | 8/1965 | Perrine |

(Continued)

FOREIGN PATENT DOCUMENTS

| | | | |
|---|---|---|---|
| CN | 1747683 | A | 3/2006 |
| CN | 1863566 | A | 11/2006 |

(Continued)

OTHER PUBLICATIONS

Office Action issued Dec. 17, 2013 in JP Application No. 2012-529808.

(Continued)

*Primary Examiner* — Emily Schmidt
(74) *Attorney, Agent, or Firm* — Panitch Schwarze Belisario & Nadel LLP

(57) ABSTRACT

Extension rods of a telescoping assembly (TSA) may be assembled in a single direction. The rods may optionally be threaded together from a reverse extended configuration. The rods may optionally resist disattachement during extension. The inner rod may optionally included a leading fastener and/or the outer rod may optionally include a rear fastener. Each rod may optionally be molded as a single piece. End caps may optionally be added to the TSA after extension of the rods. An end cap may optionally include a rotation stopper. In some embodiments the TSA may include a supporting shoulder.

26 Claims, 13 Drawing Sheets

(51) Int. Cl.
  *A61M 5/168* (2006.01)
  *A61M 5/172* (2006.01)

(56) References Cited

U.S. PATENT DOCUMENTS

| | | | |
|---|---|---|---|
| 3,212,685 A | 10/1965 | Swan et al. | |
| 3,794,028 A | 2/1974 | Mueller et al. | |
| 3,994,295 A | 11/1976 | Wulff | |
| 4,195,636 A | 4/1980 | Behnke | |
| 4,218,724 A | 8/1980 | Kaufman | |
| 4,273,122 A | 6/1981 | Whitney et al. | |
| 4,300,554 A | 11/1981 | Hessberg et al. | |
| 4,403,987 A | 9/1983 | Gottinger | |
| 4,435,173 A | 3/1984 | Siposs et al. | |
| 4,465,478 A | 8/1984 | Sabelman et al. | |
| 4,565,543 A | 1/1986 | Bekkering et al. | |
| 4,585,439 A | 4/1986 | Michel | |
| 4,599,082 A | 7/1986 | Grimard | |
| 4,601,702 A | 7/1986 | Hudson | |
| 4,685,903 A | 8/1987 | Cable et al. | |
| 4,698,055 A | 10/1987 | Sealfon | |
| 4,810,215 A | 3/1989 | Kaneko | |
| 4,850,966 A | 7/1989 | Grau et al. | |
| 4,867,743 A | 9/1989 | Vaillancourt | |
| 4,886,499 A | 12/1989 | Cirelli et al. | |
| 4,919,596 A | 4/1990 | Slate et al. | |
| 4,929,241 A | 5/1990 | Kulli | |
| 4,950,246 A | 8/1990 | Muller | |
| D322,671 S | 12/1991 | Szwarc | |
| 5,109,850 A | 5/1992 | Blanco et al. | |
| 5,112,317 A | 5/1992 | Michel | |
| 5,131,816 A | 7/1992 | Brown et al. | |
| 5,190,521 A | 3/1993 | Hubbard et al. | |
| 5,254,096 A | 10/1993 | Rondelet et al. | |
| 5,300,045 A | 4/1994 | Plassche, Jr. | |
| 5,342,313 A | 8/1994 | Campbell et al. | |
| 5,348,544 A | 9/1994 | Sweeney et al. | |
| 5,366,498 A | 11/1994 | Brannan et al. | |
| 5,383,865 A | 1/1995 | Michel | |
| 5,478,315 A | 12/1995 | Brothers et al. | |
| 5,482,446 A | 1/1996 | Williamson et al. | |
| 5,496,274 A | 3/1996 | Graves et al. | |
| 5,501,665 A | 3/1996 | Jhuboo et al. | |
| 5,505,709 A | 4/1996 | Funderburk et al. | |
| 5,562,686 A | 10/1996 | Sauer et al. | |
| 5,593,390 A | 1/1997 | Castellano et al. | |
| 5,616,132 A | 4/1997 | Newman | |
| 5,643,218 A | 7/1997 | Lynn et al. | |
| 5,645,955 A | 7/1997 | Maglica | |
| 5,647,853 A | 7/1997 | Feldmann et al. | |
| 5,662,678 A | 9/1997 | Macklin | |
| 5,672,160 A | 9/1997 | Osterlind et al. | |
| 5,690,618 A | 11/1997 | Smith et al. | |
| D393,314 S | 4/1998 | Meisner et al. | |
| 5,766,186 A | 6/1998 | Faraz et al. | |
| 5,795,675 A | 8/1998 | Maglica | |
| 5,800,420 A | 9/1998 | Gross et al. | |
| 5,807,375 A | 9/1998 | Gross et al. | |
| 5,814,020 A | 9/1998 | Gross | |
| 5,836,920 A | 11/1998 | Robertson | |
| 5,848,991 A | 12/1998 | Gross et al. | |
| 5,851,197 A | 12/1998 | Marano et al. | |
| 5,858,001 A | 1/1999 | Tsals et al. | |
| 5,858,008 A | 1/1999 | Capaccio | |
| 5,868,710 A | 2/1999 | Battiato et al. | |
| 5,931,814 A | 8/1999 | Alex et al. | |
| 5,941,850 A | 8/1999 | Shah et al. | |
| 5,948,392 A | 9/1999 | Haslwanter et al. | |
| 5,954,697 A | 9/1999 | Srisathapat et al. | |
| 5,957,895 A | 9/1999 | Sage et al. | |
| 5,968,011 A | 10/1999 | Larsen et al. | |
| 5,993,423 A | 11/1999 | Choi | |
| 6,004,297 A | 12/1999 | Steenfeldt-Jensen et al. | |
| 6,033,245 A | 3/2000 | Yamkovoy | |
| 6,033,377 A | 3/2000 | Rasmussen et al. | |
| 6,064,797 A | 5/2000 | Crittendon et al. | |
| 6,074,369 A | 6/2000 | Sage et al. | |
| 6,186,982 B1 | 2/2001 | Gross et al. | |
| 6,200,289 B1 | 3/2001 | Hochman et al. | |
| 6,200,296 B1 | 3/2001 | Dibiasi et al. | |
| 6,224,569 B1 | 5/2001 | Brimhall | |
| 6,248,093 B1 | 6/2001 | Moberg | |
| 6,277,095 B1 | 8/2001 | Kriesel et al. | |
| 6,277,098 B1 | 8/2001 | Klitmose et al. | |
| 6,277,099 B1 | 8/2001 | Strowe et al. | |
| 6,287,283 B1 | 9/2001 | Ljunggreen et al. | |
| 6,293,925 B1 | 9/2001 | Safabash et al. | |
| 6,302,633 B1 * | 10/2001 | Poe | F16B 5/0233 411/318 |
| 6,336,729 B1 | 1/2002 | Pavelle et al. | |
| 6,345,968 B1 | 2/2002 | Shupe | |
| 6,377,848 B1 | 4/2002 | Garde et al. | |
| 6,391,005 B1 | 5/2002 | Lum et al. | |
| 6,423,029 B1 | 7/2002 | Elsberry | |
| D465,026 S | 10/2002 | May et al. | |
| 6,458,102 B1 | 10/2002 | Mann et al. | |
| 6,485,461 B1 | 11/2002 | Mason et al. | |
| 6,485,465 B2 | 11/2002 | Moberg et al. | |
| 6,500,150 B1 | 12/2002 | Gross et al. | |
| 6,503,231 B1 | 1/2003 | Prausnitz et al. | |
| 6,511,336 B1 | 1/2003 | Turek et al. | |
| 6,517,517 B1 | 2/2003 | Farrugia et al. | |
| D471,274 S | 3/2003 | Diaz et al. | |
| D471,983 S | 3/2003 | Hippolyte et al. | |
| 6,558,351 B1 | 5/2003 | Steil et al. | |
| 6,589,229 B1 | 7/2003 | Connelly et al. | |
| 6,595,956 B1 | 7/2003 | Gross et al. | |
| 6,595,960 B2 | 7/2003 | West et al. | |
| 6,645,181 B1 | 11/2003 | Lavi et al. | |
| 6,652,482 B2 | 11/2003 | Hochman | |
| 6,656,158 B2 | 12/2003 | Mahoney et al. | |
| 6,656,159 B2 | 12/2003 | Flaherty | |
| 6,659,980 B2 | 12/2003 | Moberg et al. | |
| 6,673,033 B1 | 1/2004 | Sciulli et al. | |
| 6,679,862 B2 | 1/2004 | Diaz et al. | |
| 6,689,118 B2 | 2/2004 | Alchas et al. | |
| 6,699,218 B2 | 3/2004 | Flaherty et al. | |
| 6,722,916 B2 | 4/2004 | Buccinna et al. | |
| 6,743,211 B1 | 6/2004 | Prausnitz et al. | |
| 6,749,587 B2 | 6/2004 | Flaherty | |
| 6,752,787 B1 | 6/2004 | Causey, III et al. | |
| 6,768,425 B2 | 7/2004 | Flaherty et al. | |
| 6,786,890 B2 | 9/2004 | Preuthun et al. | |
| 6,800,071 B1 | 10/2004 | McConnell et al. | |
| 6,805,687 B2 | 10/2004 | Dextradeur et al. | |
| 6,824,529 B2 | 11/2004 | Gross et al. | |
| 6,843,782 B2 | 1/2005 | Gross et al. | |
| 6,854,620 B2 | 2/2005 | Ramey | |
| 6,905,298 B1 | 6/2005 | Haring | |
| 6,908,452 B2 | 6/2005 | Diaz et al. | |
| 6,960,192 B1 | 11/2005 | Flaherty et al. | |
| 6,997,727 B1 | 2/2006 | Legrady et al. | |
| 7,001,360 B2 | 2/2006 | Veasey et al. | |
| 7,034,223 B2 | 4/2006 | Fan et al. | |
| 7,048,715 B2 | 5/2006 | Diaz et al. | |
| 7,060,054 B2 | 6/2006 | Nissels | |
| 7,060,059 B2 | 6/2006 | Keith et al. | |
| 7,066,909 B1 | 6/2006 | Peter et al. | |
| 7,097,637 B2 | 8/2006 | Triplett et al. | |
| 7,128,727 B2 | 10/2006 | Flaherty et al. | |
| 7,144,384 B2 | 12/2006 | Gorman et al. | |
| D544,092 S | 6/2007 | Lewis | |
| 7,225,694 B2 * | 6/2007 | Said | F16H 25/20 74/89.35 |
| 7,247,149 B2 | 7/2007 | Beyerlein | |
| 7,250,037 B2 | 7/2007 | Shermer et al. | |
| 7,267,669 B2 | 9/2007 | Staunton et al. | |
| 7,291,132 B2 | 11/2007 | DeRuntz et al. | |
| 7,291,159 B2 | 11/2007 | Schmelzeisen-Redeker et al. | |
| 7,303,549 B2 | 12/2007 | Flaherty et al. | |
| 7,344,385 B2 | 3/2008 | Chen | |
| 7,364,570 B2 | 4/2008 | Gerondale et al. | |
| 7,390,314 B2 | 6/2008 | Stutz, Jr. et al. | |
| 7,407,493 B2 | 8/2008 | Cane' | |

(56) References Cited

U.S. PATENT DOCUMENTS

| | | |
|---|---|---|
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,920,374 B2 | 12/2014 | Bokelman et al. |
| 9,061,104 B2 | 6/2015 | Daniel |
| 9,061,110 B2 | 6/2015 | Avery et al. |
| 9,089,475 B2 | 7/2015 | Fangrow |
| 9,089,641 B2 | 7/2015 | Kavazov |
| 2001/0025168 A1 | 9/2001 | Gross et al. |

(56) References Cited

U.S. PATENT DOCUMENTS

| | | |
|---|---|---|
| 2001/0041869 A1 | 11/2001 | Causey et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0161332 A1 | 10/2002 | Ramey |
| 2002/0169215 A1 | 11/2002 | Meng |
| 2003/0009133 A1 | 1/2003 | Ramey |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2004/0010207 A1 | 1/2004 | Flaherty et al. |
| 2004/0049161 A1 | 3/2004 | Shearn |
| 2004/0092873 A1* | 5/2004 | Moberg .............. A61M 5/1456 604/131 |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0186441 A1 | 9/2004 | Graf et al. |
| 2004/0260233 A1 | 12/2004 | Garibotto et al. |
| 2005/0033234 A1 | 2/2005 | Sadowski et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Dilanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173439 A1 | 8/2006 | Thorne et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0167912 A1 | 7/2007 | Causey et al. |
| 2007/0185449 A1 | 8/2007 | Mernoe |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |

(56) References Cited

U.S. PATENT DOCUMENTS

| | | |
|---|---|---|
| 2011/0178472 A1 | 7/2011 | Cabiri |
| 2011/0201998 A1 | 8/2011 | Pongpairochana et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | |
|---|---|---|
| CN | 101090749 A | 12/2007 |
| CN | 201941304 U | 8/2011 |
| CN | 102186733 A | 9/2011 |
| DE | 1064693 B | 9/1959 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 1530979 A1 | 5/2005 |
| EP | 1666080 A1 | 6/2006 |
| EP | 2060606 A1 | 5/2009 |
| EP | 2498589 A1 | 9/2012 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |
| WO | 02072182 A1 | 9/2002 |
| WO | 03090833 A1 | 11/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2005072795 A2 | 8/2005 |
| WO | 2006037434 A1 | 4/2006 |
| WO | 2006069380 A1 | 6/2006 |
| WO | 2006102676 A1 | 9/2006 |
| WO | 2006104806 A2 | 10/2006 |
| WO | 2007051563 A1 | 5/2007 |
| WO | 2007056504 A1 | 5/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2010089313 A1 | 8/2010 |
| WO | 2011075105 A1 | 6/2011 |
| WO | 2011090955 A1 | 7/2011 |
| WO | 2011090956 A2 | 7/2011 |
| WO | 2011156373 A1 | 12/2011 |
| WO | 2012032411 A2 | 3/2012 |
| WO | 2012040528 A1 | 3/2012 |

(56) References Cited

FOREIGN PATENT DOCUMENTS

| WO | 2012160157 A1 | 11/2012 |
| WO | 2014179774 A1 | 11/2014 |

OTHER PUBLICATIONS

Office Action issued Dec. 10, 2013 in CN Application No. 201180006567.4.
Office Action issued Jan. 8, 2014 in U.S. Appl. No. 13/521,167 by Cabiri.
U.S. Appl. No. 29/479,307 by Norton, filed Jan. 14, 2014.
U.S. Appl. No. 14/593,051 by Gross, filed Jan. 9, 2015.
Office Action issued Nov. 5, 2014 in U.S. Appl. No. 13/643,470 by Alon.
U.S. Appl. No. 14/553,399 by Cabiri, filed Nov. 25, 2014.
Office Action issued Nov. 2, 2014 in CN Application No. 201180006571.0.
Office Action issued Nov. 21, 2014 in U.S. Appl. No. 13/472,112 by Cabiri.
Office Action issued Nov. 21, 2014 in U.S. Appl. No. 13/429,840 by Cabiri.
Int'l Preliminary Report on Patentability issued Nov. 27, 2014 in Int'l Application No. PCT/US2013/039465.
U.S. Appl. No. 14/683,193 by Cabiri, filed Apr. 10, 2015.
Office Action issued Feb. 20, 2015 in U.S. Appl. No. 13/521,181 by Cabiri.
Office Action issued Feb. 24, 2015 in U.S. Appl. No. 14/258,661 by Cabiri.
U.S. Appl. No. 14/638,525 by Filman, filed Mar. 4, 2015.
Extended European Search Report issued Feb. 23, 2015 in EP Application No. 14166596.8.
Office Action issued Mar. 10, 2015 in U.S. Appl. No. 13/643,470 by Alon.
Office Action issued Mar. 10, 2015 in U.S. Appl. No. 12/244,666 by Gross.
Extended European Search Report issued Feb. 23, 2015 in EP Application No. 14166591.9.
Office Action issued Mar. 10, 2015 in CN Application No. 201180006567.4.
Office Action issued Mar. 31, 2015 in JP Application No. 2012-550068.
Daikyo Crystal Zenith® polymer, Manufactured by Daikyo Seiko, Ltd.
Copaxone®, Manufactured by Teva Pharmaceutical Industries Ltd.
Int'l Search Report issued May 13, 2009 in Int'l Application No. PCT/IL2008/001312.
Int'l Preliminary Report on Patentability issued Apr. 7, 2010 in Int'l Application No. PCT/IL2008/001312; Written Opinion.
Int'l Search Report issued Apr. 26, 2010 in Int'l Application No. PCT/US2009/069552.
Office Action issued Apr. 5, 2010 in U.S. Appl. No. 12/244,666.
Office Action issued Sep. 21, 2010 in U.S. Appl. No. 12/244,666.
Office Action issued Apr. 5, 2010 in U.S. Appl. No. 12/244,688.
Office Action issued Sep. 2, 2010 in U.S. Appl. No. 12/244,688.
Office Action issued Sep. 30, 2010 in U.S. Appl. No. 12/689,250.
Int'l Search Report issued Jan. 12, 2011 in Int'l Application No. PCT/US2010/048556; Written Opinion.
International Preliminary Report on Patentability issued on Jul. 5, 2011 in International Application No. PCT/US2009/069552; Written Opinion.
Office Action issued Jul. 13, 2011 in U.S. Appl. No. 12/559,563.
Int'l Preliminary Report on Patentability issued Sep. 1, 2011 in Int'l Application No. PCT/US2010/048556.
Office Action issued Sep. 6, 2011 in U.S. Appl. No. 12/345,818.
Office Action issued Feb. 21, 2012 in U.S. Appl. No. 12/689,249.
Int'l Search Report issued Jun. 17, 2011 in Int'l Application No. PCT/US2011/021604.
Int'l Search Report issued Oct. 12, 2011 in Int'l Application No. PCT/US2011/021605.
Office Action issued Oct. 28, 2011 in U.S. Appl. No. 12/615,828.
Int'l Search Report issued Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action issued May 16, 2012 in U.S. Appl. No. 12/615,828.
Office Action issued Jul. 2, 2012 in U.S. Appl. No. 13/272,555.
Office Action issued May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.
Int'l Preliminary Report on Patentability issued Aug. 2, 2012 in Int'l Application No. PCT/US2011/021604.
U.S. Appl. No. 13/643,470 by Alon, filed Oct. 25, 2012.
U.S. Appl. No. 13/733,516 by Cabiri, filed Jan. 3, 2013.
Office Action issued Jan. 8, 2013 in JP Application No. 2010-527595.
Int'l Preliminary Report on Patentability issued Feb. 7, 2013 in Int'l Application No. PCT/US2011/021604.
Int'l Preliminary Report on Patentability issued Feb. 7, 2013 in Int'l Application No. PCT/US2011/021605.
English translation of an Office Action issued Jan. 30, 2013 in CN Application No. 200880117084.X.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,017 by Cabiri, filed Apr. 30, 2013.
U.S. Appl. No. 14/258,661 by Cabiri, filed Apr. 22, 2014.
Int'l Search Report and Written Opinion issued Jan. 7, 2014 in Int'l Application No. PCT/US2013/065211.
Office Action issued May 23, 2014 in U.S. Appl. No. 13/472,112 by Cabiri.
Int'l Preliminary Report on Patentability issued May 14, 2015 in Int'l Application No. PCT/US2013/065211.
Office Action issued May 7, 2015 in JP Application No. 2012-550069.
Office Action issued May 13, 2015 in CN Application No. 201380025566.3.
U.S. Appl. No. 14/715,791 by Cabiri, filed May 19, 2015.
U.S. Appl. No. 14/725,009 by Bar-El, filed May 29, 2015.
Office Action issued May 1, 2015 in U.S. Appl. No. 14/638,525 by Filman.
Office Action issued Jun. 4, 2015 in U.S. Appl. No. 13/667,739 by Cabiri.
Office Action issued Jun. 3, 2014 in JP Application No. 2010-527595.
Office Action issued Jul. 7, 2014 in U.S. Appl. No. 12/244,666 by Gross.
Int'l Search Report and Written Opinion issued Jul. 31, 2014 in Int'l Application No. PCT/US2014/033598.
Office Action issued Jul. 31, 2015 in U.S. Appl. No. 13/521,181 by Cabiri.
Office Action issued Aug. 13, 2015 in U.S. Appl. No. 14/553,399 by Cabiri.
Int'l Preliminary Report on Patentability issued Jul. 16, 2015 in Int'l Application No. PCT/US2013/078040.
Notice of Allowance issued Aug. 24, 2015 in U.S. Appl. No. 29/479,307 by Norton.
Int'l Search Report and Written Opinion issued Jul. 26, 2013 in Int'l Application No. PCT/US2012/039465.
Int'l Search Report and Written Opinion issued Aug. 5, 2013 in Int'l Application No. PCT/US2013/033118.
U.S. Appl. No. 13/964,651 by Gross, filed Aug. 12, 2013.
Office Action issued Aug. 15, 2013 in CN Application No. 200880117084.X.
Extended European Search Report issued Aug. 7, 2014 in EP Application No. 1417477.4.
Office Action issued Aug. 6, 2014 in EP Application No. 11 707 942.6.
Office Action issued Sep. 2, 2014 in JP Application No. 2012-550069.
Office Action issued Sep. 2, 2014 in JP Application No. 2012-550068.
Office Action issued Aug. 26, 2014 in CN Application No. 201180006567.4.

(56) References Cited

OTHER PUBLICATIONS

Int'l Preliminary Report on Patentability issued Oct. 9, 2014 in Int'l Application No. PCT/US2013/033118.
Office Action issued Oct. 9, 2014 in U.S. Appl. No. 13/873,335.
Office Action issued Oct. 9, 2013 in IL Application No. 208634.
Office Action issued Nov. 5, 2013 in JP Application No. 2010-527595.
Office Action issued Sep. 29, 2013 in CN Application No. 201080040968.7.
Office Action issued Nov. 4, 2013 in EP Application No. 11 709 234.6.
U.S. Appl. No. 14/193,692 by Gross, filed Feb. 28, 2014.
Office Action issued Feb. 4, 2014 in EP Application No. 11 707 942.6.
English translation of an Office Action issued Mar. 5, 2014 in CN Application No. 200880117084.X.
Int'l Search Report and Written Opinion issued Apr. 3, 2014 in Int'l Application No. PCT/US2013/078040.
Extended European Search Report issued Mar. 27, 2014 in EP Application No. 14154717.4.
Office Action issued Feb. 28, 2014 in CN Application No. 201180006571.0.
Office Action issued Sep. 9, 2015 in U.S. Appl. No. 13/643,470 by Alon.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action issued Sep. 30, 2015 in U.S. Appl. No. 13/667,739 by Cabiri.
Partial European Search Report issued Nov. 24, 2015 in EP Application No. 14166592.7.
Office Action issued Dec. 1, 2015 in CN Application No. 201410289204.1.
Extended European Search Report issued Mar. 8, 2016 in EP Application No. 14166592.7.

* cited by examiner

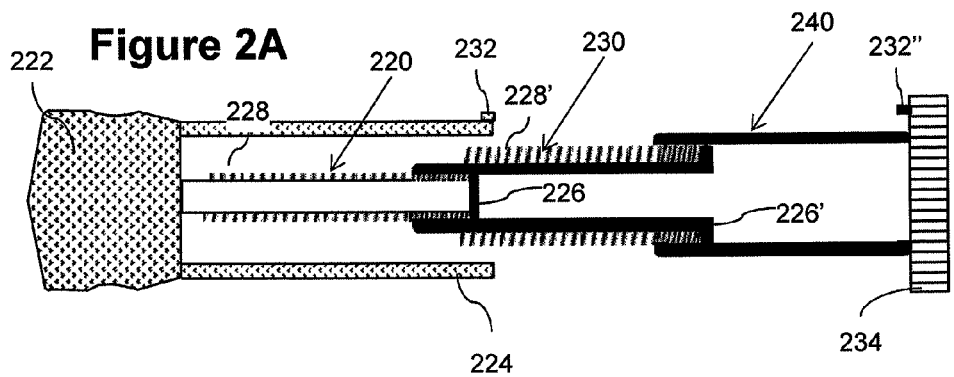
Figure 2A
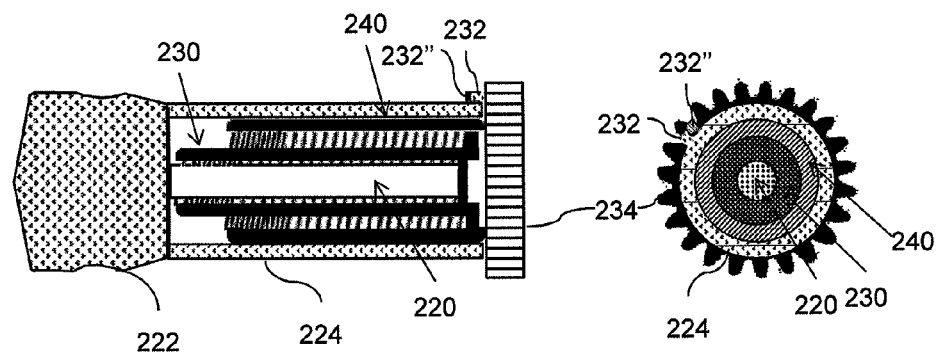
Figure 2B
Figure 2B'
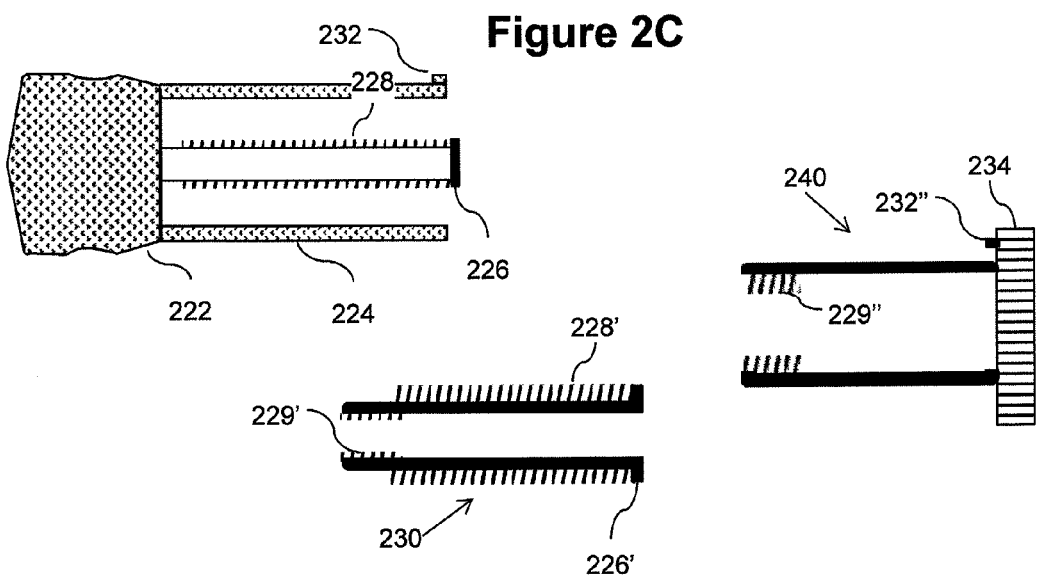
Figure 2C

DISENGAGEMENT RESISTANT TELESCOPING ASSEMBLY AND UNIDIRECTIONAL METHOD OF ASSEMBLY FOR SUCH

CROSS-REFERENCE TO RELATED APPLICATIONS

This application is related to U.S. application Ser. No. 13/874,017, entitled "APPARATUSES FOR SECURING COMPONENTS OF A DRUG DELIVERY SYSTEM DURING TRANSPORT AND METHODS OF USING SAME," to the same applicants and filed on Apr. 30, 2013, the disclosure of which is incorporated herein by reference.

BACKGROUND OF THE INVENTION

The present invention, in some embodiments thereof, relates to a high reliability telescoping assembly (TSA) and method of assembly for such and, more particularly, but not exclusively, to a unidirectional assembly method for a disengagement resistant TSA from molded parts.

U.S. Pat. No. 7,967,795 to the instant applicant (Cabiri) discloses A cartridge interface assembly including a driving plunger including an outer shaft, and a driver including an inner shaft, the inner shaft mating with an intermediate shaft, the intermediate shaft mating with the outer shaft, so that the shafts are movable telescopically with respect to one another, wherein rotation of the driver causes the driving plunger to advance in a direction away from the driver.

U.S. Patent Application Publication No. 2009/0093792 to Gross discloses an apparatus for administering a substance to a subject. A vial contains the substance and a stopper is disposed within the vial and is slidably coupled to the vial. A first threaded element is (a) rotatable with respect to the vial and (b) substantially immobile proximally with respect to the vial during rotation of the first threaded element. A second threaded element is threadedly coupled to the first threaded element. At least a distal end of the second threaded element is substantially non-rotatable with respect to the vial, and the distal end of the second threaded element defines a coupling portion that couples the second threaded element to the stopper. The first threaded element, by rotating, linearly advances the stopper and at least the distal end of the second threaded element toward a distal end of the vial.

International Patent Application Publication No. WO/2011/090956 to the instant applicant (Cabiri) disclosed a cartridge interface assembly characterized by a driving plunger including an outer shaft, and a driver including an inner shaft movable telescopically with respect to the outer shaft, wherein rotation of the driver causes the driving plunger to advance in a direction away from the driver, and wherein the cartridge interface assembly is inserted in a cartridge in which a plunger is slidingly disposed, and rotation of the driver causes the driving plunger to advance distally in the cartridge until abutting against the plunger.

U.S. Pat. No. 8,157,769 to the present instant applicant (Cabiri) discloses A cartridge insertion assembly including apparatus with a pathway formed therein, a cartridge insertable into the pathway, the cartridge including a cartridge coupling element connectable to an activation mechanism disposed in the apparatus operative to cause a substance contained in the cartridge to be metered out of the cartridge, and a door pivoted to the apparatus that includes a door coupling element arranged with respect to the cartridge such that when the door is in a fully closed position, the door coupling element couples the cartridge coupling element with a coupling element of the activation mechanism.

U.S. Pat. No. 7,225,694 to Said, discloses a telescopic actuator that has a lead screw and one or more concentric or tiered screws. Each screw has one or more tangential interference stop features such as stop cogs. As the lead screw is rotated, it translates out of the concentric screws. As the lead screw reaches its maximum extension, a tangential interference stop feature on the lead screw tangentially contacts a tangential interference stop feature on the concentric screw with which the lead screw is threadably engaged. Upon tangential contact, the associated concentric screw rotates in unison with the lead screw. When there are additional concentric screws, as each concentric screw reaches its maximum extension, the system of tangential contacting of tangential interference stop features causes the other concentric screws to extend out in sequential fashion.

Additional background art includes U.S. Pat. No. 8,220,349, U.S. Pat. No. 6,494,005, U.S. Pat. No. 6,435,048, and U.S. Pat. No. 6,382,039.

BRIEF SUMMARY OF THE INVENTION

According to an aspect of some embodiments of the present invention there is provided a method of assembling a telescoping screw including: threading a leading end of an inner rod into a rear end of a mid rod; also threading a leading end of the mid rod into a rear end of an outer rod so that the leading end of the inner rod is accessible from an leading end of the outer rod, and fastening a first end cap onto the leading end of the inner rod.

According to some embodiments of the invention, the method may further include extending the telescoping screw by further threading the inner rod to extend the leading end of the inner rod out of the leading end of the outer rod.

According to some embodiments of the invention, the method may further include driving the extending by rotating the first end cap.

According to some embodiments of the invention, the method may further include also fastening a second end cap onto the rear end of the outer rod.

According to some embodiments of the invention, the method may further include driving extension of the telescoping screw by rotating the second end cap.

According to some embodiments of the invention, the method may further include preventing an unthreading of the telescoping screw by providing a rotational stopper to limit unthreading rotation of the first end cap with respect to the outer rod According to some embodiments of the invention, the rotational stopper includes an interference element between first end cap and to the outer rod.

According to some embodiments of the invention, the method may further include preventing an unthreading of the telescoping screw by providing a rotational stopper to limit unthreading rotation of the second end cap with respect to the inner rod.

According to some embodiments of the invention, the method may further include pushing a load by extending the telescopic screw.

According to some embodiments of the invention, the load includes a plunger of a syringe and the method further includes discharging a drug from the syringe by the pushing of the plunger.

According to some embodiments of the invention, the method may further include extending the telescoping screw by further threading the mid rod to extend a leading end of the mid rod out of the leading end of the outer rod.

According to some embodiments of the invention, the method may further include providing a fastener on the leading end of the inner rod.

According to some embodiments of the invention, the inner rod is molded in one piece with the fastener.

According to some embodiments of the invention, the method may further include blocking over extension of the middle rod from the outer rod by a protrusion on the rear end of the middle rod.

According to some embodiments of the invention, the middle rod is molded in one piece with the protrusion.

According to some embodiments of the invention, the method may further include blocking over extension of the inner rod from the mid rod by a protrusion on a rear end of the inner rod.

According to some embodiments of the invention, the inner rod is molded in one piece with the protrusion.

According to some embodiments of the invention, the method may further include supporting the telescoping screw against an inside wall of a syringe via a shoulder.

According to an aspect of some embodiments of the present invention there is provided a telescoping assembly including: an outer rod including a rear fastener and a leading internal thread; a middle rod including an external thread fitting the internal thread of the outer rod, a rear protrusion wider than the internal thread of the outer rod and a leading internal thread; and an inner rod including an external thread fitting the internal thread of the middle rod and a rear protrusion wider than the internal thread of the middle rod.

According to some embodiments of the invention, each of the inner rod, mid rod and outer rod is molded in a single piece.

According to some embodiments of the invention, the telescoping assembly further includes a first end cap including a matching fastener for fastening to the rear fastener.

According to some embodiments of the invention, the telescoping assembly further includes a stopper for preventing dethreading of telescoping assembly, the stopper including an interference element on the first end cap for preventing rotation in a contracting direction of the inner rod with respect to the first end cap.

According to some embodiments of the invention, the inner rod further includes a leading fastener.

According to some embodiments of the invention, the telescoping assembly further includes a second end cap including a matching fastener for fastening to the leading fastener.

According to some embodiments of the invention, the telescoping assembly further includes a stopper for preventing dethreading of telescoping assembly, the stopper including an interference element on the second end cap for preventing rotation in a contracting direction of the outer rod with respect to the second end cap.

According to some embodiments of the invention, the telescoping assembly further includes a shoulder fitting into a bore of a syringe and rotatable with respect to the syringe the shoulder supporting the telescoping assembly.

According to some embodiments of the invention, the inner rod, the mid rod and the outer rod are all threaded in a first direction, and the telescoping assembly further includes an end cap with a thread in an opposite direction.

According to some embodiments of the invention, the respective pitch of threading of each of the inner rod, the mid rod and the outer rod is adjusted to produce the same magnitude of linear motion per rotation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-D are schematic cross-sectional illustrations of a TSA in an extended state, a contracted state, an exploded view, and a reverse extended state, in accordance with an exemplary embodiment of the invention;

DETAILED DESCRIPTION OF THE INVENTION

Figure 1:
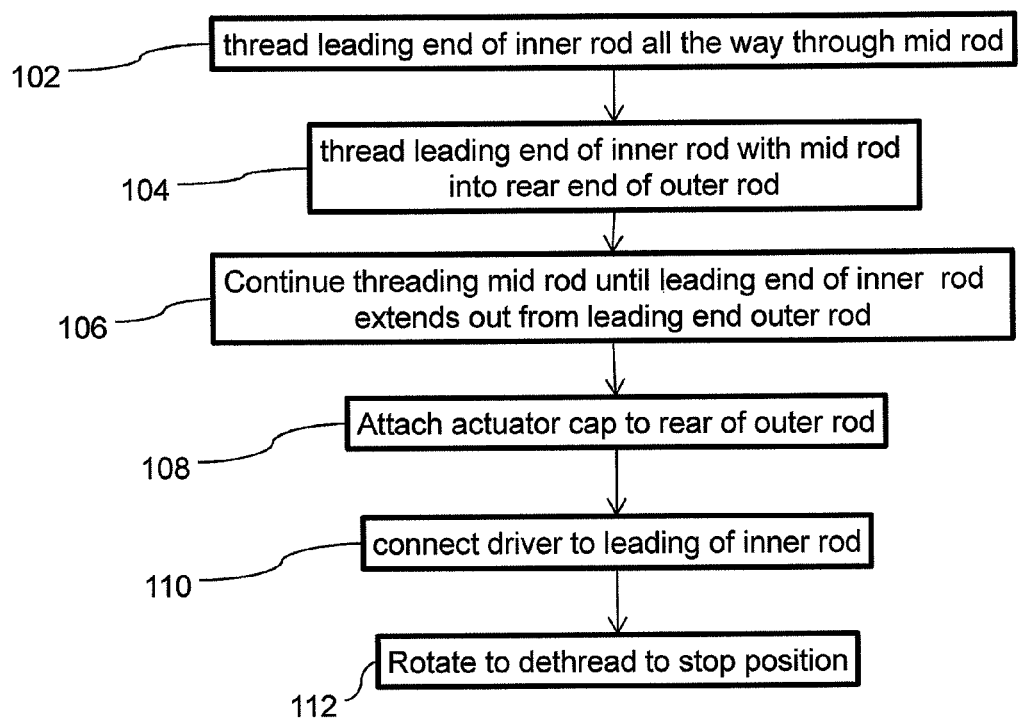
FIG. 1 is a flowchart showing a method of assembling a telescoping assembly (TSA), in accordance with an exemplary embodiment of the invention.

The present invention, in some embodiments thereof, relates to a high reliability telescoping assembly (TSA) and method of assembly for such and, more particularly, but not exclusively, to a unidirectional assembly method for a disengagement resistant TSA from molded parts.

Overview

1. Simple Assembly of a TSA

An aspect of some embodiments of the invention relates to providing a TSA that is assembled in a simple manner. Optionally, assembly may be unidirectional. Unidirectional assembly may include, for example, insertion of all or most extension rods from the same end of the TSA. Unidirectional assembly may include, for example, threading all extension rods the same direction. Optionally, assembly may be accomplished without reversing orientation of the assembly during assembly and/or adding other complimentary work such as welding, riveting, plastic deformation Etc.

In some embodiments, a series of extension rods may be threaded together. For example for each rod in the series, a leading end of an interior rod may be threaded may be threaded through into a rear end of a more exterior rod. As used herein, the term/phrase leading end means the end of a TSA from which the inner rod projects in the extended state. As used herein, the term/phrase rear end means the end of a TSA from which the outer rod projects in the extended state. As used herein, the term/phrase threading means screwing the more interior rod towards the leading direction. As used herein, the term/phrase de-threading means screwing the more interior rod towards the rear of the outer rod. Optionally, the leading end of the most inner rod may include a fastener and/or the rear end of the most external rod may include a fastener.

Developing an effective drug therapy and treatment includes more than simply finding an effective molecule. It includes combination of a safe drug within a suitable container and/or delivery system.

One possible failure is premature detaching and or disengaging of a threaded rod from a TSA of the delivery system. Typically, a rod may have a drive mechanism or an actuator on one end and a thread on the other end. A rod that is screwed to the assembly from the screw side may possibly be disengaged from the assembly in reverse direction. As a TSA is extended, the order of extension may sometimes become inverted causing the threads of one element to become disengaged before the assembly is completely extended. As result, the TSA may fail to extend completely resulting in failure to deliver a full dose of the drug.

Another source of failure of a TSA is errors and/or imprecision in the TSA assembly process. For example, a complex assembly processes and/or low precision modification of the parts during assembly may decrease the reliability of a TSA.

2. Disengagement Resistant TSA

An aspect of some embodiments of the invention relates to providing a TSA that resists disengagement and/or detaching of extension rods upon extension. For example, an internal rod of the TSA may include a flange on its rear end. The flange may prevent disengagement from a more outer rod. Alternatively or additional the flange may be replaced by a protrusion of a different geometry.

3. Use of Molded Parts

An aspect of some embodiments of the invention relates to providing a TSA that is assembled from molded parts. In some embodiments, molding provides highly precise part geometries. Molded parts may optionally be assembled with minimal modifications during assembly. For example, the assembly of the TSA may be include minimal or no adhesion of parts, and/or changing of part geometries by heat and/or ultrasonic means and/or by force (for example by crimping). The molded parts may optionally include features to facilitate proper orientation. The molded parts may optionally include built in connectors and/or fasteners (for example snaps, latches, catches, hooks, clasps and the like). In some embodiments that parts may be molded of plastic. For example plastic may include low friction materials. Example of such materials includes for example CELANEX® (for example 2405 MT) available from TICONA and Delrin® (for example 100AL NC010) by DuPont™.

In some embodiments an internal rod may be molded in a single piece with the rear flange and/or projections. The flange and/or projection may optionally impeded unintentional disengagement of the rod. In some embodiments a part may be molded in a single piece with a fastener. In some embodiments a part may be molded in a single piece with a stopper.

4. Stoppers

An aspect of some embodiments of the invention relates to a stopper that may stop rotation of a TSA. For example a protrusion molded into an end cap may interact with a corresponding protrusion molded into an adjoining end of an extension rod to stop rotation of the rod and/or of a plurality of rods at a predefined point. For example, the stopper may prevent thread lock and or dethreading of the TSA after the TSA reaches a contracted state

5. Shoulder Support

An aspect of some embodiments of the invention relates to an end cap shoulder which supply support to a TSA in a syringe. For example a driver may include a shoulder which is inserted into the bore of a syringe to provide support for the outer end of the TSA: The shoulder may optionally rotate in the syringe bore. Optionally, the space for the shoulder may be counter sunk into the syringe flange. Countersinking the shoulder may save space in the syringe bore for the TSA.

Exemplary Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

1. Reverse Assembly and Installation of End Caps

In some embodiments, some or all of the extension rods of the assembly may optionally be supplied disassembled from the end caps. For example, the some or all of the rods and/or end caps may include fasteners. The extension rods may optionally be supplied with flanges inhibiting disassembly due to overextension. For example, an internal rod may have a flange on a rear end. The flanges and/or fasteners may optionally be intrinsic. For example, the rods and/or caps may be molded in a single piece with the fasteners and/or flanges.

In some embodiments, some or all of the extension rods assembled together by reverse extension. For example, a leading end of an internal rod may be threaded into a rear end of a more external rod. For example, the internal rod may be threaded from a disassembled (reverse extended) position through its contracted position out the leading end of a mating rod to an extended position. In some embodiments, threading from the reverse extended position may be necessary because flanges which prevent the rods from disattaching in the extended state may also prevent attaching the rods in the extended state and threading them to the contracted state.

In some embodiments, a fastener may be supplied on a leading end of an inner rod. Once the leading end of an inner rod extends beyond the mating rod, an end cap (for example a driver and/or an actuator) may be fastened to the fastener. Optionally a stopper may be supplied. For example the stopper may block dethreading back to the reverse extended position and/or may prevent thread lock resulting from collision between a rod and an end cap.

Referring now to the drawings, FIG. 1 illustrates an exemplary method for assembling a TSA. In some embodiments, the leading end of an inner rod may be threaded 102 into the rear end of a mid rod. Optionally the leading end of the inner rod may be threaded all the way through a mid rod until the leading end of the inner rod protrudes from the leading end of the mid rod.

In some embodiments, the leading end of the inner rod along with the middle rod may be threaded 104 into a rear end of an outer rod. Threading 104 be continued 106 until the leading end of the inner rod protrudes out the leading end of the outer rod. Optionally the assembly may include only two rods and/or more than three rods (for example four, five, six or more rods). In some embodiments, regardless of the number of rods, the assembly of rods may have a fastener of the inner rod protruding from the leading end and a fastener of an outer rod protruding from the rear end (for example see FIG. 3H).

In some embodiments, an actuator cap (for example cap 324 of FIG. 3I) may be attached 108 to the fastener of the outer rod. For example, an actuator cap may include a syringe plunger and/or a fitting to attach to a syringe plunger. Examples of syringe plungers actuated by telescopic assemblies can be found for example in International Patent Application Publication No. WO/2011/090956 by the instant applicant (Cabiri) and/or U.S. Patent Application Publication No. 2009/0093792 to Gross which are herein incorporated in their entirety by reference.

In some embodiments, a driver cap (for example cap 334 of FIG. 3K) may be attached 110 to the fastener of the inner rod. For example, a driver cap may include a gear for rotating the inner rod in order to extend and/or contract the TSA.

In some embodiments, after assembly, the TSA may be dethreaded 112 to a stop position. Optionally, the TSA may include one or more stoppers. For example a pair of stoppers on the two end caps (for example the drive cap and the actuator cap) may meet at a predefined point in the contraction of the TSA and prevent further relative rotation in the dethreading direction of the inner rod with respect to the outer rod thereby preventing further contraction (for example see stoppers 332 and 332" of FIGS. 3K and 3M).

2. Components of a TSA and Their Interconnection

In some embodiments, a TSA may be simple assembled unidirectionally from a reverse extended position. The assembled TSA may optionally resist dis-assembly by extension.

Referring now to the drawings, FIG. 2A illustrates an exemplary schematic representation of a TSA in an extended state. One end the assembly may, for example, be connected to an actuator mount 224 and/or an actuator 222 (for example actuator 222 may include a plunger for discharging medicine from a syringe). The other end may, optionally, be connected to a driver 234 (for example driver 234 may include a gear to rotate a threaded rod (for example an outer rod 240) thereby extending and/or contracting the TSA).

In some embodiments expansion and contraction of the TSA may be effected by a series of threaded rods. For example, an inner rod 220 may be threaded into a rear end of a mid rod 230 which may optionally be threaded into a rear end of an outer rod 240. In the exemplary embodiment of FIGS. 2A-E, rods 220, 230, and/or 240 may optionally include interior threads (for example threads 229' and/or 229" (see FIG. 2C)) and/or exterior threads (for example threads 228 and/or 228' (see FIG. 2C)).

In some embodiments a rod may include a member to prevent disengagement of the rod during extension of the TSA. For example inner rod 220 includes a rear flange 226 and mid rod 230 includes a rear flange 226'. When rod 220 reaches full extension, flange 226 contacts interior threads 229' of mid rod 230 preventing further extension (see FIG. 2A). When rod 230 reaches full extension, flange 226' contacts interior threads 229" of outer rod 230 preventing further extension (see FIG. 2A). Alternatively or additionally a flange (for example flange 226 and/or 226') may be include a protrusion of any geometry and not necessarily and annular ring.

Figure 2D:
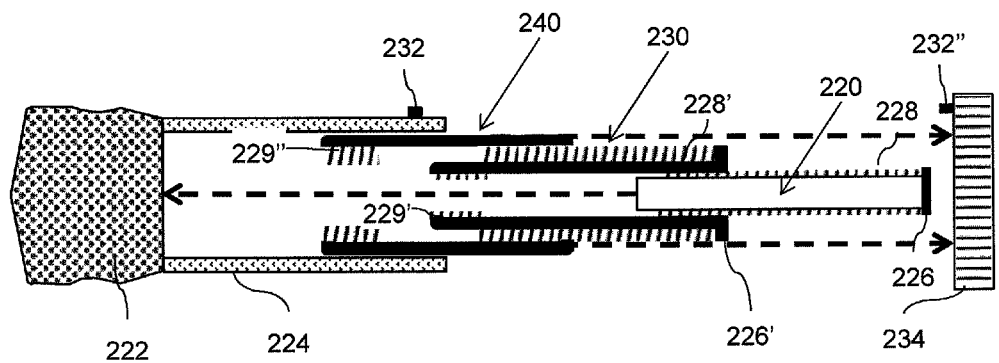

In some embodiments, a TSA may include stop element. For example, FIG. 2B illustrate a cutaway side view and a cutaway end on view of the TSA of FIGS. 2A-D in a fully contracted state. A protrusions 232 on driver 234 contacts a matching protrusion 232" on actuator mount 224 inhibiting further relative rotation in the dethreading direction between driver 234 and actuator mount 224. Optionally thereby further dethreading may be prevented between inner rod 220 and outer rod 240.

FIG. 2C illustrates the exemplary TSA of FIGS. 2A-D with rods 220, 230, and 240 disassembled. Flanges 226 and 226' which prevent disengagement of rods may also prevent assembly of rods in the extended state. Driver 234 and end cap 232 may prevent assembly in the opposite direction.

FIG. 2D illustrates the exemplary embodiment of a TSA of FIGS. 2A-D in a reverse extended configuration (extension rods 220, 230 and 240 are in the opposite order of extended state of FIG. 2A). In some embodiments, assembly of the TSA may start from the reverse extended state. Assembly may optionally proceed unidirectionally, some and/or all of the extension rods being sequentially inserted into the assembly in the same direction. For example, from the reverse extended state, a leading end of inner rod 220 may be threaded through the rear end of mid rod 230. For example the leading end mid rod 230 and inner rod 220, may be threaded in the same direction together through the rear end of outer rod 240.

In some embodiments, after threading together the extension rods, end caps may be attached. For example, actuator mount 224 and/or actuator 222 may be attached to a leading end of inner rod 220 (as illustrated by the broken arrow in the left side of FIG. 2D). For example, after threading together the extension rods (for example rods 220, 230, and 240) an end cap (for example driver 234) may be attached to a rear end of outer rod 240 (as illustrated, for example, by the dual dashed arrows on the right side of FIG. 2D).

Figure 2E:
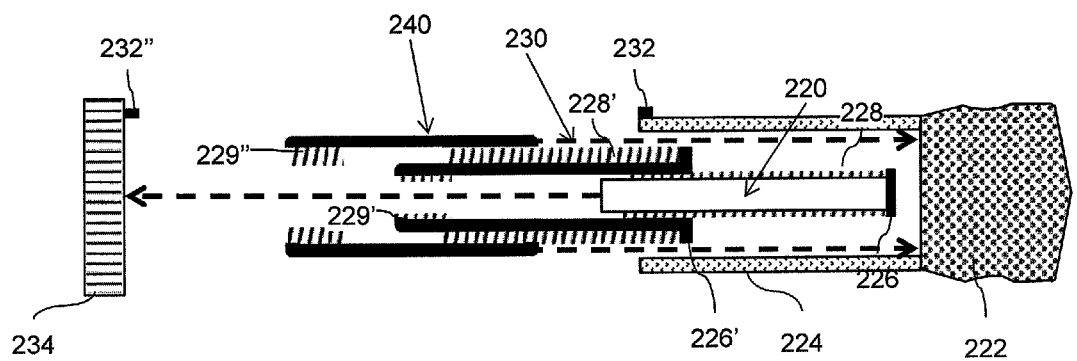
FIG. 2E is schematic cross-sectional illustration of an alternative embodiment of a TSA in an a reverse extended state, in accordance with an exemplary embodiment of the invention.

FIG. 2E illustrates assembly of an alternative exemplary embodiment of a TSA in the reverse extended state. The exemplary embodiment of FIG. 2E has end caps reversed (actuator 222 is connected to outer rod 240 and drive 234 is connected to inner rod 220) with respect to the embodiment of FIG. 2D.

3. An Example of Assembly of an External TSA with Snap on End Caps and Shoulder Support FIGS. 3A-M illustrate an exemplary embodiment of an out of syringe unidirectional assembled TSA having optional snap on end caps and a shoulder support. Snap on end caps may optionally allow connecting end caps without modifying, gluing, or melting parts during assembly. A TSA may optionally include a shoulder support. The shoulder support may be inserted into a syringe bore. For example the shoulder may add to the mechanical stability of the telescoping assembly during operation. The shoulder may optionally hold an extension rod in proper relation to a bore (for example of a syringe). The shoulder may optionally rotate with respect to the syringe bore.

Figure 3A:
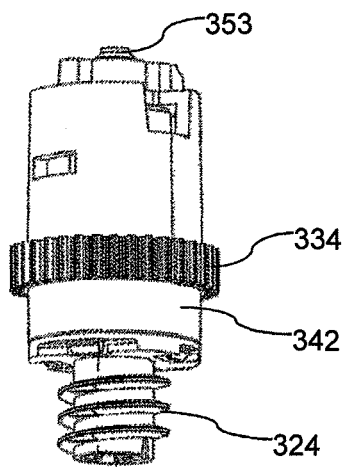
FIGS. 3A-B are perspective views of an alternative embodiment of a TSA in contracted, extended states respectively, in accordance with an exemplary embodiment of the invention.

Referring now to the drawings, FIG. 3A illustrates perspective views of an alternative exemplary embodiment of a PSA in a contracted state. The two end caps can be seen; including for example a driver 334 and/or an actuator mount 324. The actuator mount may optionally include a screw thread to attach to a syringe plunger. The driver may optionally include a shoulder 342 configured to fit into a syringe bore as seen for example in FIGS. 3C,D and 5A,B. The shoulder may support the TSA against movements (for example sideways translation) caused by forces on the driver.

Figure 3B:
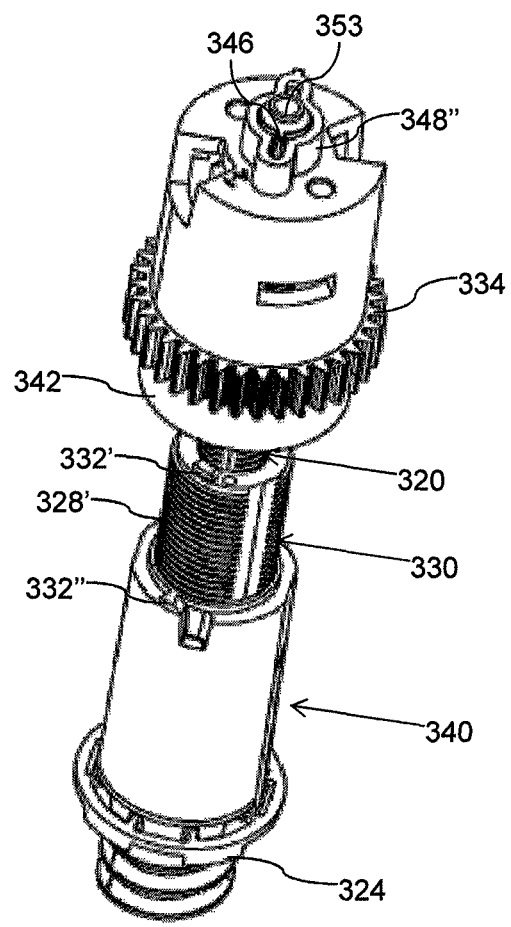

FIG. 3B illustrates a perspective view of an alternative exemplary embodiment of a TSA in an extended state. Along with the end caps, extension rods including an inner rod 320, a mid rod 330 and an outer rod 340, are visible in FIG. 3B. External screw 328' is also shown on the mid rod. Also shown in FIG. 3B are optional stoppers including projections 332' and 332" which fit into recesses (not shown) in driver 334 to stop relative rotation of outer rod 340 and/or mid rod 330 with respect to driver 334 and/or inner rod 320 as the TSA reaches a contracted state.

Figure 3C:
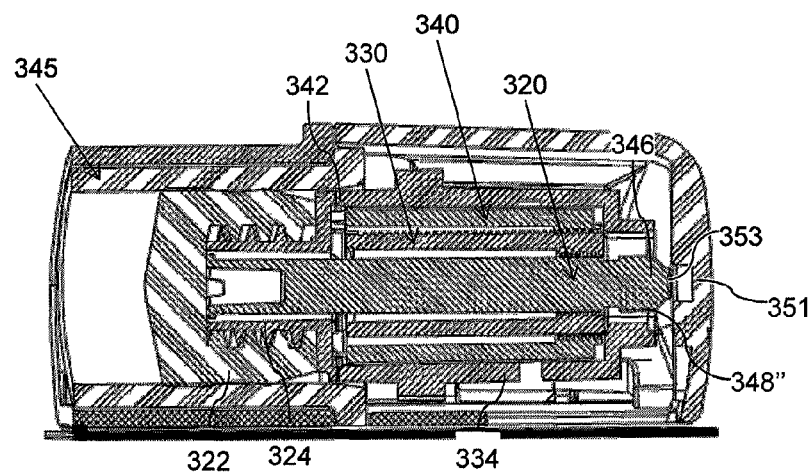
FIGS. 3C-D are cross sectional views of an alternative embodiment of a TSA installed in a syringe in contracted and extended states respectively, in accordance with an exemplary embodiment of the invention.

FIG. 3C illustrates a cutaway view of an alternative exemplary embodiment of a TSA installed into a syringe 345 in a contracted state. Shoulder 342 is at least partially inserted into the bore of syringe 345. In the example of FIG. 3C, in the contracted state, most of the length of the TSA projects out of syringe 345. For example, in the example of FIG. 3C, mid rod 330 and/or outer rod 340 sit entirely outside syringe 345. For example, in the example of FIG. 3C, inner rod 320 is mostly outside of syringe 345 with a small portion extending inside syringe 345.

In the example of FIG. 3C, support for the TSA is supplied on the distal end by shoulder 342 which extends into the bore of syringe 345 and is supported by the inner walls of the syringe. Optionally, syringe 345 may and/or shoulder 342 (and/or all of driver 334) may be made of low friction materials. For example, the inner walls of syringe 345 may support shoulder 342 against lateral forces (preventing lateral translation). Nevertheless, shoulder 342 may optionally be able to rotate within the syringe bore.

In the example of FIG. 3C, support for the TSA is supplied on the proximal end by an axel 353 extending from the proximal end of inner rod 320 out of driver 334 into a hub 351. Hub 351 may for example, be part of a door of a patch injector for example as described in U.S. Pat. No. 8,157,769 to the instant applicant (Cabiri) which is herein incorporated in their entirety by reference. Optionally, hub 351 and/or axel 353 (and/or all of inner rod 320) may be made of low friction materials. For example, hub 351 may support axel 353 against lateral forces (preventing lateral translation). Nevertheless, axel 353 may optionally be able to rotate within hub 351.

Figure 3D:
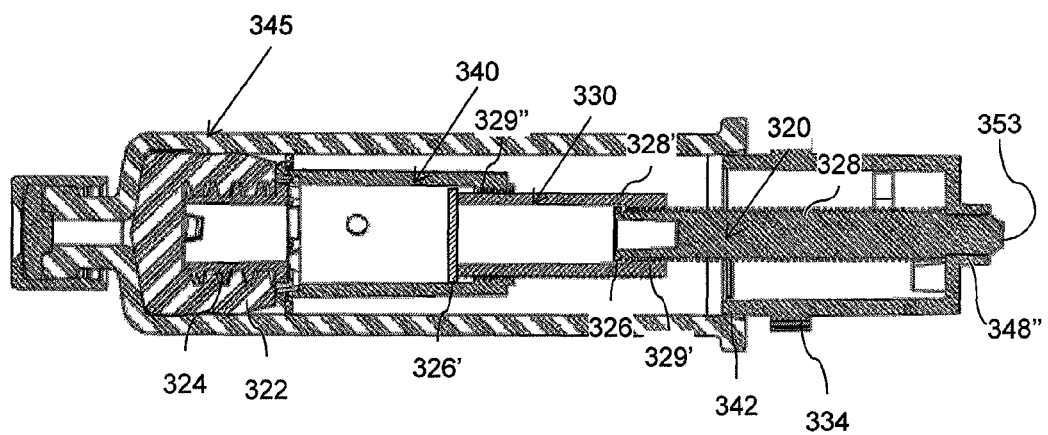

Referring now to the figures, FIG. 3D is a cutaway view of an alternative exemplary embodiment of a TSA installed into a syringe in an extended state. Flanges 326 and 326' are illustrated on rods 320 and 330 respectively. Flanges 326 and 326' may optionally restrain respective extension rods 320 and 330 from disengaging upon extension. For example flange 326 may prevent extension rod 320 from disengaging from inner teeth 329' of extension rod 330 upon extension. For example flange 326' may prevent extension rod 320 from disengaging from inner teeth 329" of extension rod 330 upon extension. In FIGS. 3C and 3D, actuator mount 324 is screwed into a plunger 322.

Figure 3E:
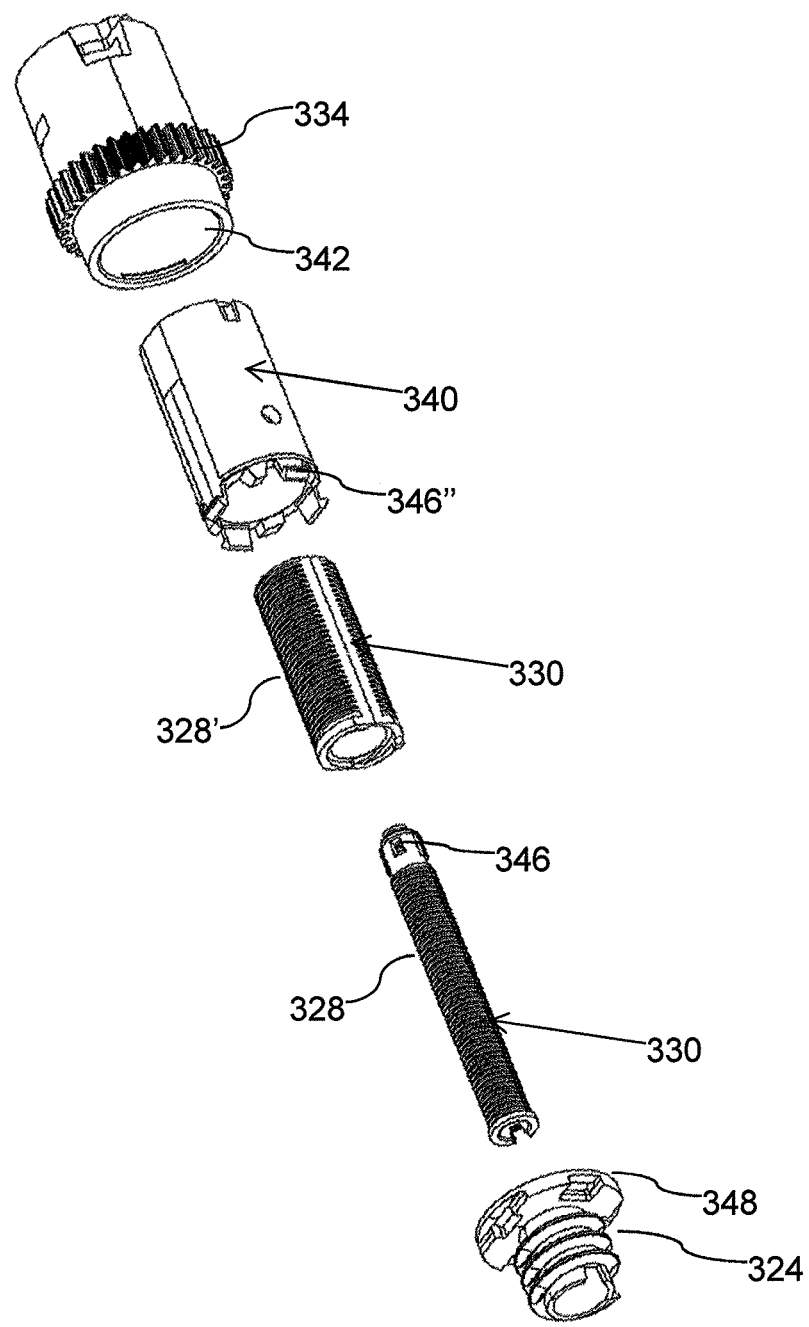
FIG. 3E is an exploded reverse extended view of an alternative embodiment of a TSA, in accordance with an exemplary embodiment of the invention.
Figure 3F:
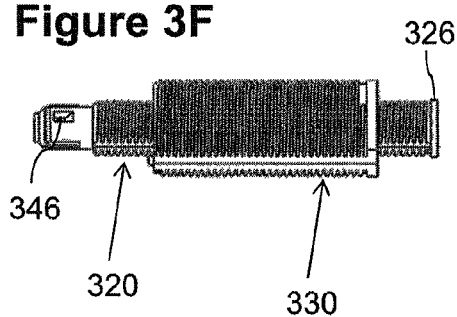
FIGS. 3F-M are perspective views of steps of assembling an alternative embodiment of a TSA, in accordance with an exemplary embodiment of the invention.
Figure 3G:
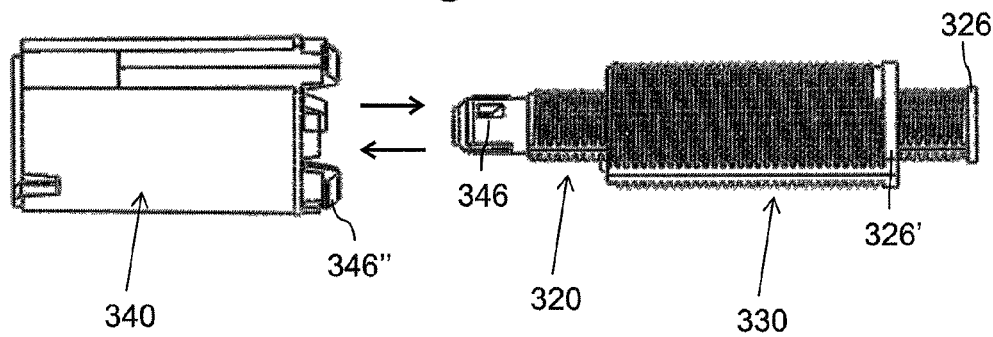
Figure 3H:
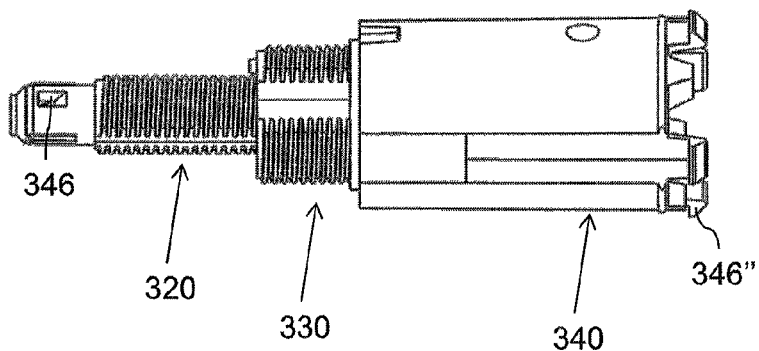

Referring now to the figures, FIGS. 3E-M illustrate assembly of an alternative exemplary embodiment of a TSA. FIG. 3E illustrates an exploded view of the exemplary embodiment of a TSA in a reverse extended configuration ready for assembly. Optionally, in the embodiment of FIG. 3E, fasteners 346 may be supplied on inner rod 320 for attachment to a matching fastener (for example a hole 348") in a driver 334. Optionally, in the embodiment of FIG. 3E, fasteners 346" may be supplied on outer rod 340 for attachment to fasteners 348 of actuator mount 324.

In the illustrative example of FIGS. 3A-M, assembly of the TSA may optionally start by threading inner rod 320 into mid rod 330, for example as illustrated in FIG. 3F. Optionally, starting from the reverse extended configuration (for example as illustrate in FIG. 3E) the leading end of inner rod 320 may be threaded all the way through mid rod 330 until it protrudes from the leading end of mid rod 330 as illustrated for example in FIG. 3F.

In the illustrative example of FIGS. 3A-M, after threaded inner rod 320 through mid rod 330, the combination may optionally be threading into outer rod 340, for example as illustrated in FIG. 3G. Optionally, threading may continue until the leading end of inner rod 320 protrudes out the far end of outer rod 340 as illustrated for example in FIG. 3H. Optionally, all rods may be assembled by threading in the same direction, from the same end of the assembly.

Figure 3I:
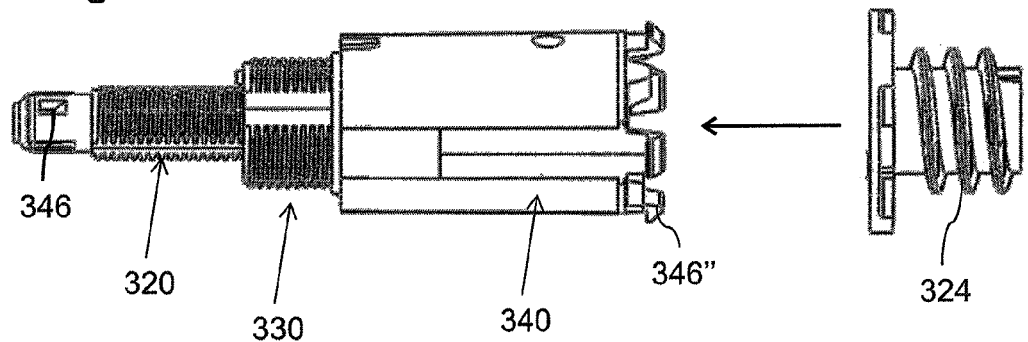
Figure 3J:
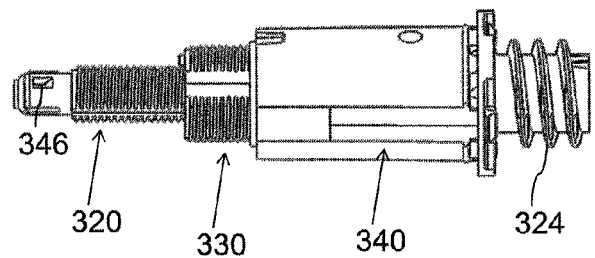

In the illustrative example of FIGS. 3A-M, after threading mid rod 330 through outer rod 340, an end cap (for example actuator mount 324) may be fastened to the rear end of outer rod 340, for example as illustrated in FIG. 3I. Optionally, fasteners may be molded into the cap and/or rod. For example, fasteners may include hooks (for example fasteners 346" and/or holes and/or eyes (for example fastener 348 and/or 348"). For example, in the exemplary embodiment of FIGS. 3A-M fasteners 346" permanently latches into fasteners 348. For example, after fastening outer rod 340 to actuator mount 324, preventing actuator mount 324 from rotating prevents outer rod 340 from rotating. Fasteners may optionally include for example flanges (for example fasteners 346), locks, rivets, buckles, clips, snaps, latches, hinges, plugs, spacers, pins, grommets, nuts, bushings, clamps, clasps and/or screws. Fasteners may be permanent and/or reversible. FIG. 3J illustrates the exemplary embodiment of FIGS. 3A-M after fastening actuator mount 324 to outer rod 340.

Figure 3K:
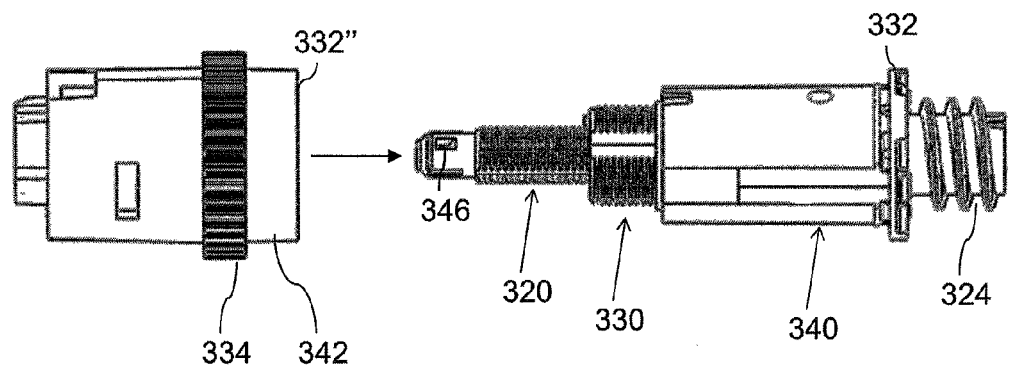
Figure 3L:
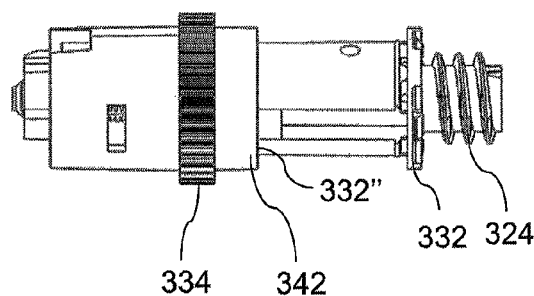

In the illustrative example of FIGS. 3A-M, after fastening actuator mount 324 to outer rod 340, an end cap (for example driver 334) may be fastened to the end of outer inner rod 320, for example as illustrated in FIG. 3K. For example, in the exemplary embodiment of FIGS. 3A-M fastener 346 permanently latches into a hole 348" of driver 334. For example, after fastening inner rod 320 to driver 334, rotating driver 334 also rotates inner rod 320. FIG. 3J illustrates the exemplary embodiment of FIGS. 3A-M after fastening driver 334 to inner rod 320.

Figure 3M:
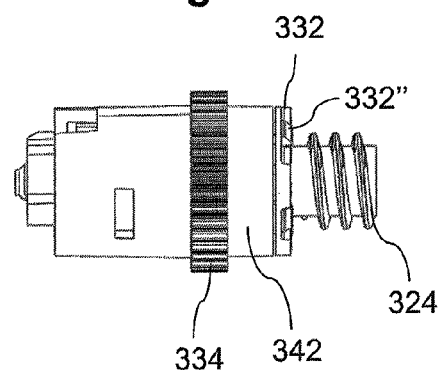

In the illustrative example of FIGS. 3A-M, after fastening driver 334 to inner rod 320, the TSA may be dethreaded together into the contracted position as illustrated in FIG. 3M. A pair of stoppers 332, 332" may stop further dethreading of driver 334 with respect to actuator cap 324 once the TSA reaches the fully closed state.

4. Alternative Embodiments

Figure 4A:
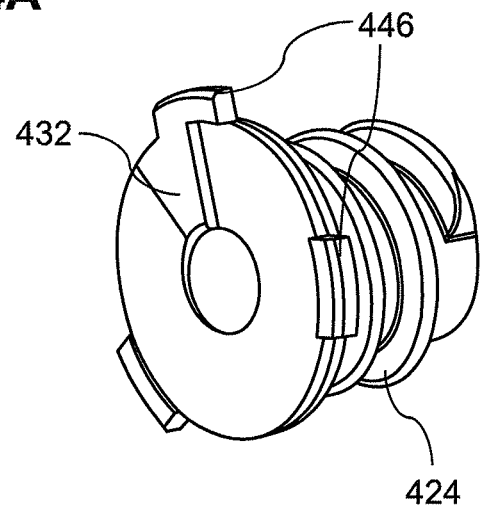
FIGS. 4A-B are perspective views of an alternative embodiment for a TSA including an alternative end cap and stopper, in accordance with an exemplary embodiment of the invention.
Figure 4B:
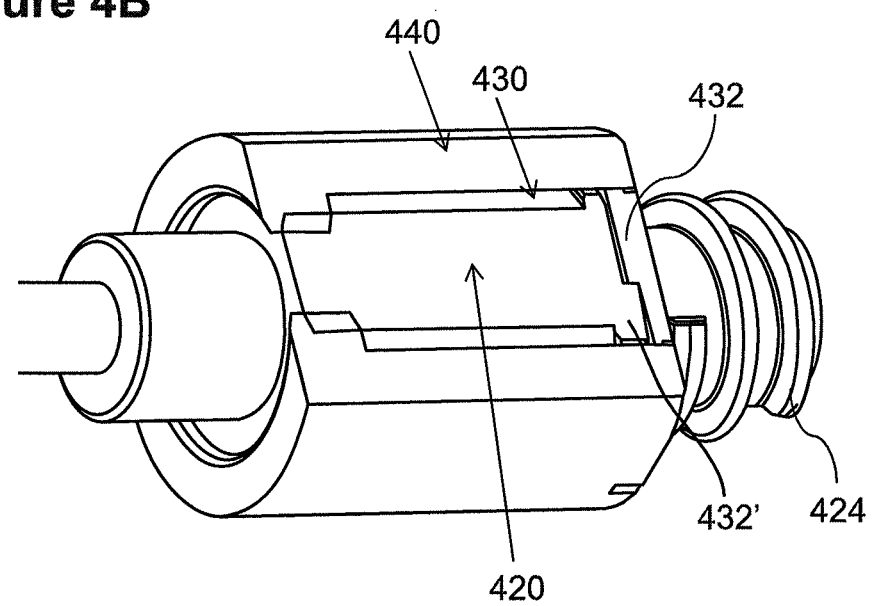

Referring now to the figures, FIGS. 4A-B illustrate an alternative embodiment of a TSA. In the exemplary embodiment of FIGS. 4A-B an actuator mount 424 serves as an end cap to an outer rod 440. Actuator mount 424, includes fasteners 446 that protrude sideways to snap into holes in the sides of outer rod 440. The exemplary embodiment of FIGS. 4A-B includes an inner rod 420 and a mid rod 430. Actuator mount 424, includes an exemplary stopper 432 which includes a ridge on the inner face of actuator mount 424. When the ridge of stopper 432 meets a ridge 432' on the base of an inner rod 420, further dethreading is prevented between inner rod 420 and actuator mount 424. Thereby further contraction of the TSA is stopped. Optionally, stoppers 432, 432', 232, 232" may stop contraction of the TSA without putting significant longitudinal force between a rod and the end piece.

Figure 5A:
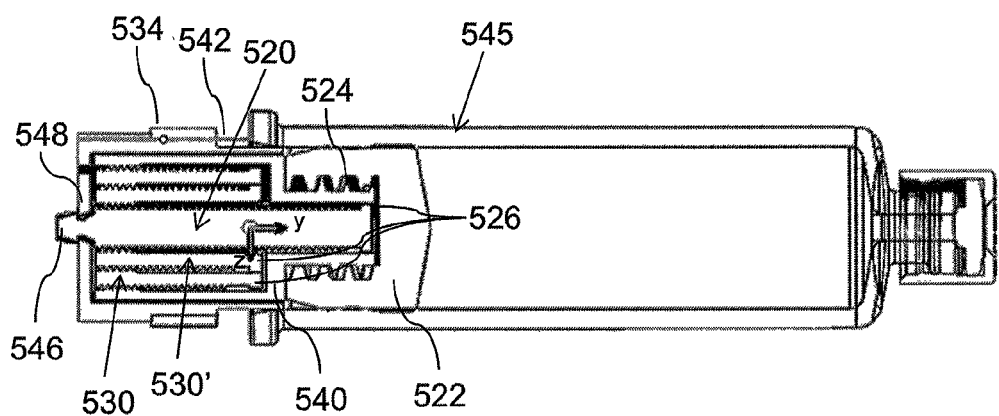
FIGS. 5A-B are cross sectional views of an another alternative embodiment of a TSA inserted into a syringe in a contracted state, in accordance with an exemplary embodiment of the invention.
Figure 5B:
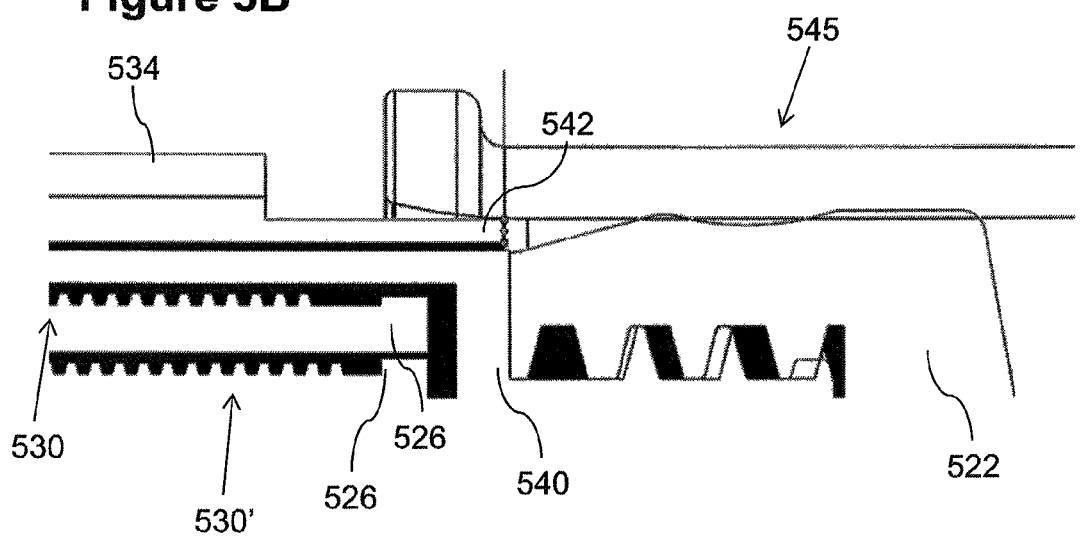
Figure 5C:
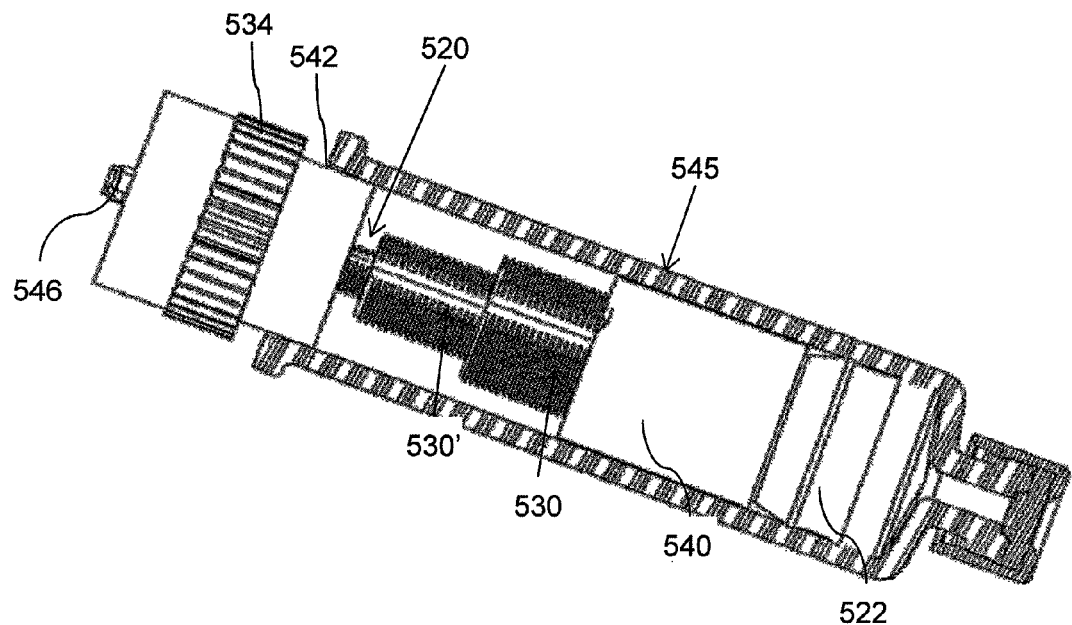
FIG. 5C is cutaway view of another alternative embodiment of a TSA inserted into a syringe, in accordance with an exemplary embodiment of the invention.

FIGS. 5A-C illustrate an alternative exemplary embodiment of a TSA. FIGS. 5A-B illustrate respective large scale and close up cutaway views of the alternative embodiment of the TSA installed into a syringe 545 in a contracted state. The embodiment of FIGS. 5A-C optionally includes four threaded extension rods, an inner rod 520, two mid rods 530, 530' and an outer rod 540. Each rod includes an optional flange 526. Outer rod 540 is optionally integrally formed with an actuator mount 524 which is screwed into a plunger 522. Inner rod 520 includes an optional fastener 546 which snaps into a hole 548 in a driver 542. Driver 534 includes an optional shoulder support 542 which is illustrated inserted into the syringe bore. FIG. 5C illustrates a perspective see through view of the alternative embodiment of a TSA inserted into syringe 545.

Figure 6:
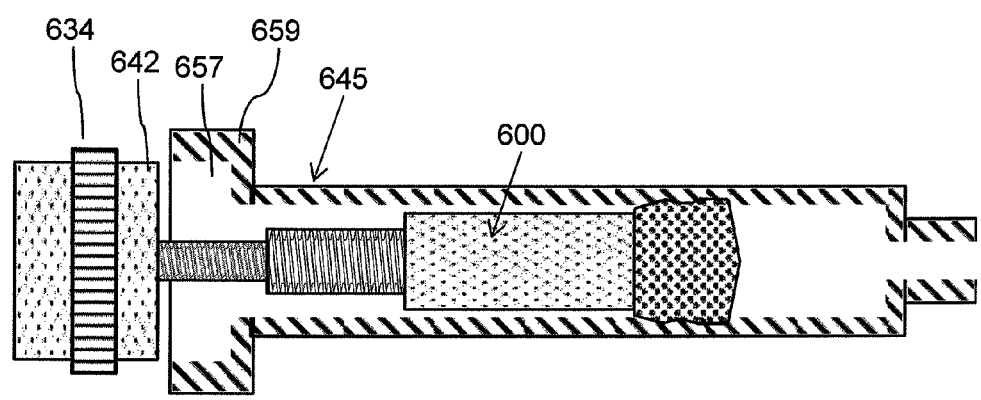
FIG. 6 is a cutaway view of an alternative embodiment of a TSA with a counter sunk shoulder support, in accordance with an exemplary embodiment of the invention.

FIG. 6 illustrates an alternative embodiment of a TSA 600 inserted into a syringe 645. The bore of syringe 645 includes an optional counter sunk cavity 657. For example, a shoulder 642 of a driver 634 may fit into counter sunk cavity. Counter sunk cavity 657 may extend into a flange 659 of syringe 645.

In some embodiments counter sunk cavity 657 may be wider than the bore of syringe 645. Optionally shoulder 642 may be wider than the bore of the syringe. Optionally making shoulder 642 wider than the syringe bore may make it possible to make more complete use of the bore for expansion rods of TSA 600.

5. State Diagram of a TSA

Figure 7:
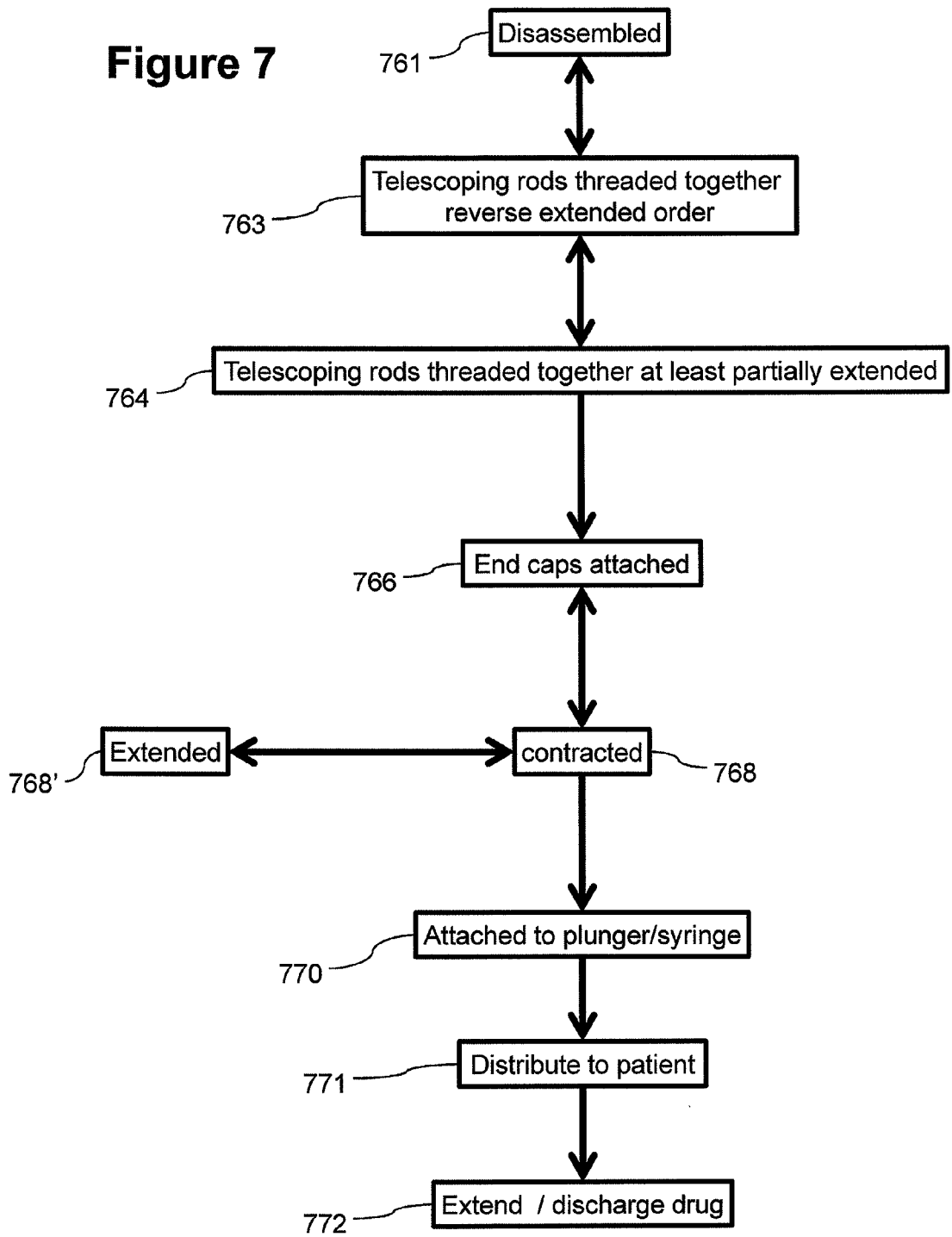
FIG. 7 is a state diagram illustrating states of a TSA, in accordance with an exemplary embodiment of the invention.

Referring now to the figures, FIG. 7 is a state diagram illustrating exemplary states of a TSA. A TSA may optionally be molded of parts in a disassembled 761 state. The parts may, for example include threaded telescoping rods. In assembly of the TSA, the rods may optionally be threaded together from a reverse extended configuration 763. The Rods may be reversibly threaded together further into a contracted and/or partially and/or fully extended 764 state.

In some embodiments, one or more end caps may be attached 766 to the extension rods. Attachment of end caps may optionally be irreversible (alternatively or additionally attachment 766 of end caps may be reversible).

In some embodiments, the end caps may inhibit return of the telescoping assembly to the reverse extended state and/or separating of the extension rods. For example, the end caps may block dethreading of the extension rods beyond the contracted state to the reverse extended state and eventually detached state. Alternatively or additionally, an end cap may include a stopper the stops movement in a certain direction of an extension rod at a certain point. For example, a stopper may prevent dethreading when an extension bar and/or the TSA reach a fully contracted state. Alternatively or additionally, the stopper may prevent further threading into super extension when the TSA reaches a fully extended state.

In some embodiments, with extension rods assembled and the end caps attached 766 the TSA can be reversibly extended 768' and/or contracted 768.

In some embodiments, the TSA will be contracted 768 and attached 770 to the plunger of a syringe. Optionally attachment 770 to a syringe may be irreversible. Alternatively or additionally attachment 700 to a syringe may be reversible.

In some embodiments, a syringe and attached TSA will be distributed 771 to a patient, for example as components of a patch injector. The patient may activate the injector, extending 772 the TSA to inject a drug. In some embodiments, extension of the TSA for discharging the drug will be irreversible. For example, after discharging the drug to the patch injector and/or the TSA and/or the syringe may be disposable. Alternatively or additionally, some or all components of a patch injector and/or TSA and/or syringe may be reusable.

6. Threading

Figure 8:
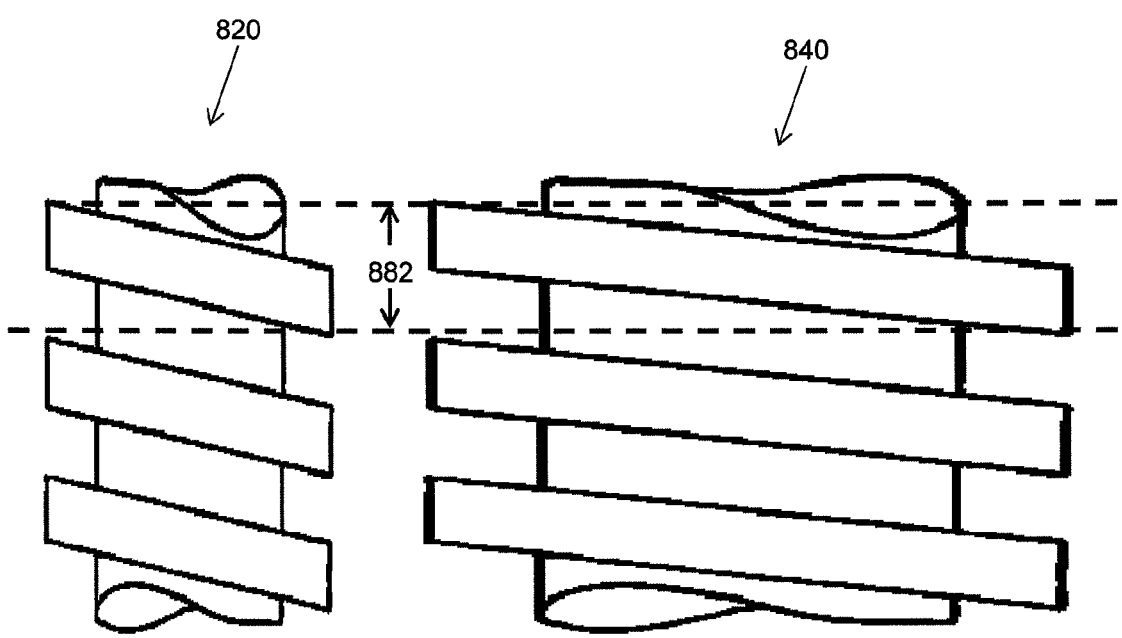
FIG. 8 is an enlarged partial plan view of the inner and outer rod threads of the TSA.

FIG. 8 illustrates threading of an inner rod 820 and an outer rod 840 in accordance with an exemplary embodiment of the invention. The pitch of the threads of each rod is adjusted so that the each rod moves the same linear distance per rotation (for example twice the distance 882) regardless of the diameter of the rod. Optionally, the linear movement of the syringe plunger and/or the quantity of medicine discharged per rotation of the driver is fixed regardless of which extension rod is active.

Extension rods 820 and 840 of FIG. 8 optionally all have a thread oriented in a single direction (for example in FIG. 8 rods 820, 840 have left hand screws). Optionally, an actuator cap (for example cap 324 of FIG. 3I) may have an opposite oriented screw thread (for example a right hand screw). Optionally, when the telescoping assembly is extended, the torque between the plunger and end cap will tend to tighten the connection between the plunger and the cap.

It is expected that during the life of a patent maturing from this application many relevant fasteners and/or other relevant parts will be developed and the scope of the terms fattener and/or other terms are intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of assembling a telescoping screw comprising:
   sliding a leading end of an inner rod through a rear end of a mid rod,
   threading an external thread of the inner rod with an internal thread proximate a leading end of the mid rod;
   sliding the leading end of said mid rod into a rear end of an outer rod,
   threading an external thread of the mid rod with an internal thread proximate, a leading end of the outer rod, such that said leading end of said inner rod is accessible from the leading end of said outer rod, and
   fastening a first end cap onto said leading end of said inner rod,
   wherein the inner rod includes a rear flange at the rear end thereof slidable through a portion of the mid rod and being wider than the internal thread of the mid-rod, thereby being prevented from further advancement upon direct contact therewith, and the mid-rod includes a rear flange at the rear end thereof slidable through a portion of the outer rod and being wider than the internal thread of the outer rod, thereby being prevented from further advancement upon direct contact therewith.

2. The method of claim 1, further comprising:
   extending the telescoping screw by further threading said inner rod to extend said leading end of said mid rod out of said leading end of said outer rod.

3. The method of claim 2, further comprising:
   driving said extending of the telescoping screw by rotating said first end cap.

4. The method of claim 1, further comprising:
   fastening a second end cap onto said outer rod.

5. The method of claim 4, further comprising:
   driving extension of the telescoping screw by rotating said second end cap.

6. The method of claim 1, further comprising:
   preventing an unthreading of the telescoping screw by providing a rotational stopper to limit unthreading rotation of said first end cap with respect to said outer rod.

7. The method of claim 6, wherein said rotational stopper includes an interference element between the first end cap and to said outer rod.

8. The method of claim 4, further comprising:
   preventing an unthreading of the telescoping screw by providing a rotational stopper to limit unthreading rotation of said second end cap with respect to said inner rod.

9. The method of claim 1, further including:
   pushing a load by extending the telescopic screw.

10. The method of claim 9, wherein said load includes a plunger of a syringe and further comprising:
    discharging a drug from said syringe by said pushing of said plunger.

11. The method of claim 1, further comprising:
    extending the telescoping screw by further threading said mid rod to extend the leading end of said mid rod out of said leading end of said outer rod.

12. The method of claim 1, further comprising:
    providing a fastener on said leading end of said inner rod.

13. The method of claim 12 wherein said inner rod is molded in one piece with said fastener.

14. The method of claim 11, further comprising:
    blocking over extension of said middle rod from said outer rod by said rear flange at said rear end of said middle rod.

15. The method of claim 14, wherein said middle rod is molded in one piece with said protrusion.

16. The method of claim 11, further comprising:
    blocking over extension of said inner rod from said mid rod by said rear flange at said rear end of said inner rod.

17. The method of claim 16, wherein said inner rod is molded in one piece with said protrusion.

18. The method of claim 1, further comprising:
    supporting the telescoping screw against an inside wall of a syringe via a shoulder.

19. A telescoping assembly comprising:
an outer rod including
a rear fastener and
an internal thread proximate a leading end thereof;
a middle rod including
an external thread fitting said internal thread of said outer rod,
a rear flange slidable through a portion of the outer rod and being wider than said internal thread of said outer rod and
an internal thread proximate a leading end thereof;
an inner rod including,
an external thread fitting said internal thread of said middle rod and
a rear flange slidable through a portion of the middle rod and being wider than said internal thread of said middle rod;
a first end cap including a matching fastener for fastening to said rear fasterner; and
a stopper for preventing dethreading of telescoping assembly, said stopper including an interference element on said first end cap for preventing rotation in a contracting direction of said inner rod with respect to said first end cap.

20. The telescoping assembly of claim 19, wherein each of said inner rod, mid rod and outer rod is molded in a single piece.

21. The telescoping assembly of claim 19, wherein said inner rod further comprises a leading fastener.

22. The telescoping assembly of claim 21, further comprising:
an end cap including a matching fastener for fastening to said leading fastener.

23. The telescoping assembly of claim 19, wherein said telescoping assembly includes a shoulder fitting into a bore of a syringe and rotatable with respect to said syringe said shoulder supporting said telescoping assembly.

24. The telescoping assembly of claim 19, wherein said inner rod, said mid rod and said outer rod are all threaded in a first orientation further including an end cap with a thread in an opposite orientation.

25. The telescoping assembly of claim 19, wherein a respective pitch of threading of each of said inner rod, said mid rod and said outer rod is adjusted to produce the same magnitude of linear motion per rotation.

26. A telescoping assembly comprising:
an outer rod including
a rear fastener and
a leading internal thread;
a middle rod including
an external thread fitting said internal thread of said outer rod,
a rear protrusion wider than said internal thread of said outer rod and
a leading internal thread; and
an inner rod including,
an external thread fitting said internal thread of said middle rod,
a rear protrusion wider than said internal thread of said middle rod and
a leading fastener;
an end cap including a matching fastener for fastening to said leading fastener; and
a stopper for preventing dethreading of telescoping assembly, said stopper including an interference element on said end cap for preventing rotation in a contracting direction of said outer rod with respect to said end cap.

* * * * *